(12) United States Patent
Farley et al.

(10) Patent No.: US 6,663,630 B2
(45) Date of Patent: Dec. 16, 2003

(54) HALO/COLLAR CERVICAL ORTHOSIS

(75) Inventors: Daniel K. Farley, Traverse City, MI (US); Anthony J. Mulac, East Jordan, MI (US); Richard L. Saunders, Lebanon, NH (US)

(73) Assignee: Spine Works LLC, Traverse City, MI (US)

( * ) Notice: Subject to any disclaimer, the term of this patent is extended or adjusted under 35 U.S.C. 154(b) by 126 days.

(21) Appl. No.: 09/949,131

(22) Filed: Sep. 7, 2001

(65) Prior Publication Data

US 2003/0050583 A1 Mar. 13, 2003

(51) Int. Cl.[7] .............................................. A61B 17/56
(52) U.S. Cl. ............................ 606/54; 606/73; 602/17; 602/37
(58) Field of Search ............................ 606/54, 56, 59, 606/61, 73, 130; 602/17, 18, 37

(56) References Cited

U.S. PATENT DOCUMENTS

| | | |
|---|---|---|
| 3,072,118 A | 1/1963 | Standerwick et al. |
| 4,475,550 A | 10/1984 | Bremer et al. |
| 4,539,979 A | 9/1985 | Bremer |
| 4,807,605 A | 2/1989 | Mattingly |
| 4,838,264 A | 6/1989 | Bremer et al. |
| 5,062,415 A | 11/1991 | Weatherby et al. |
| 5,086,757 A | 2/1992 | Lestini |
| 5,121,741 A | 6/1992 | Bremer et al. |
| 5,122,132 A | 6/1992 | Bremer |
| 5,156,588 A | * 10/1992 | Marcune et al. .............. 602/17 |
| 5,171,296 A | 12/1992 | Herman |
| 5,203,765 A | 4/1993 | Friddle, Jr. |
| 5,261,873 A | 11/1993 | Bremer et al. |
| 5,302,170 A | 4/1994 | Tweardy |
| 5,545,164 A | * 8/1996 | Howland ...................... 606/61 |
| 5,961,528 A | * 10/1999 | Birk et al. .................. 606/130 |

OTHER PUBLICATIONS

The Marlin X–2 Cervical Orthosis, Series #'s 3060–S, M, L, Johnson's Orthoepdic Designs, Inc.
The Bremer Halo System advertising material, Copyright Bremer Medical, Inc., 1994.
AccroMed advertisement, 1994.

* cited by examiner

Primary Examiner—David O. Reip
(74) Attorney, Agent, or Firm—McAndrews, Held & Malloy, Ltd.

(57) ABSTRACT

A cervical fixation system comprises a body rigidly attached to a patient's skull at one or more rigid attachment points. One method of achieving such a rigid attachment is through the use of bone screws. The bone screws may comprise a shoulder. The bone screws may further attach to the body of the cervical fixation system. Examples of possible attachment methods include the use of a quick disconnect head, and the use of a threaded body on the bone screw.

20 Claims, 6 Drawing Sheets

FIG.10
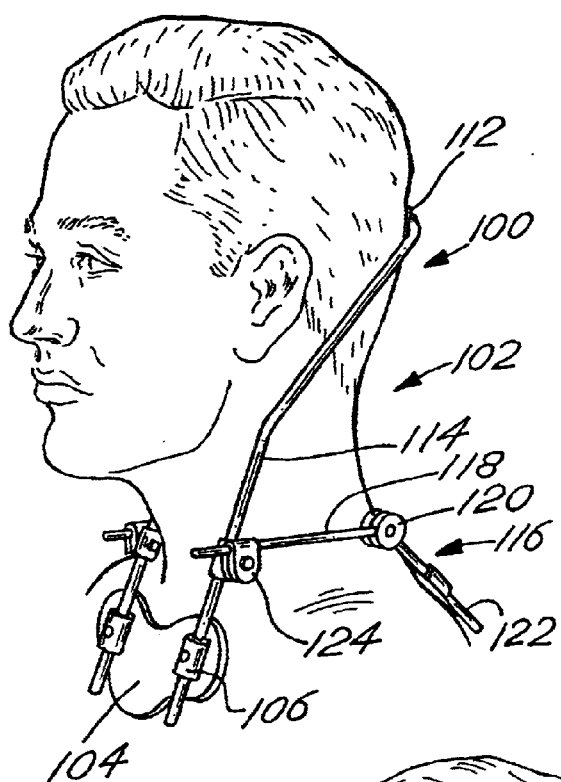
FIG.11
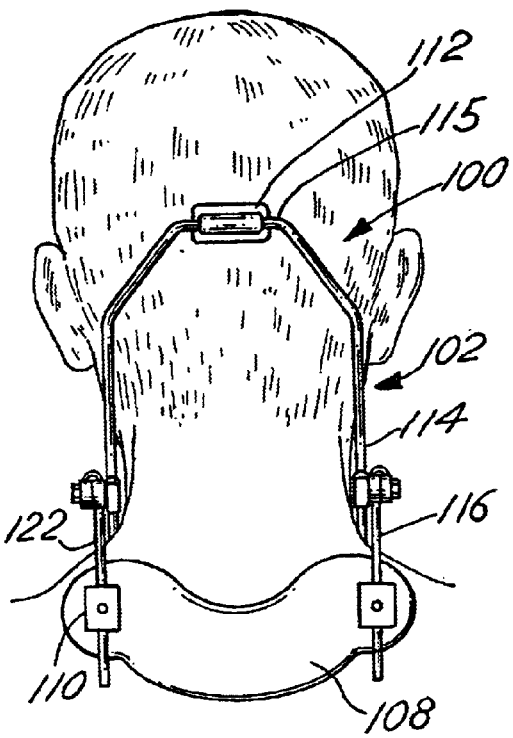
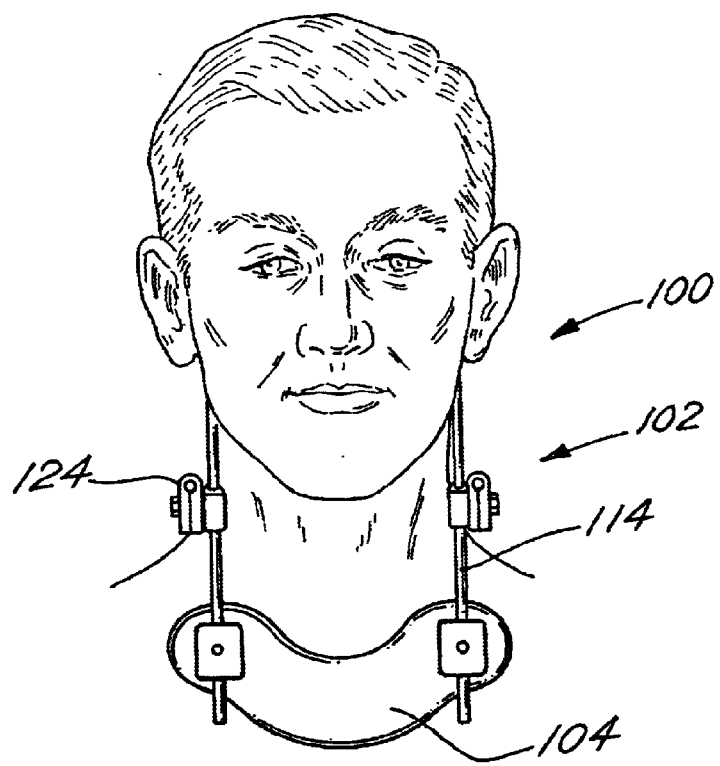
FIG.12

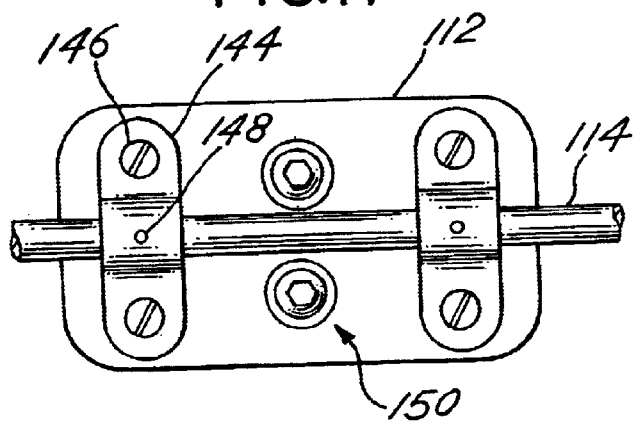
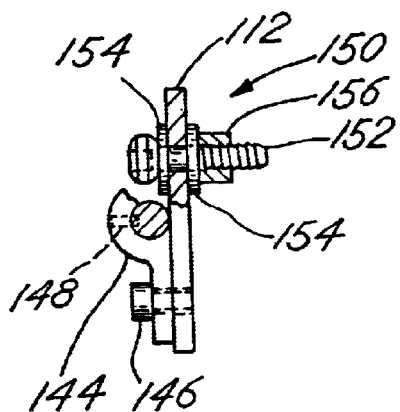
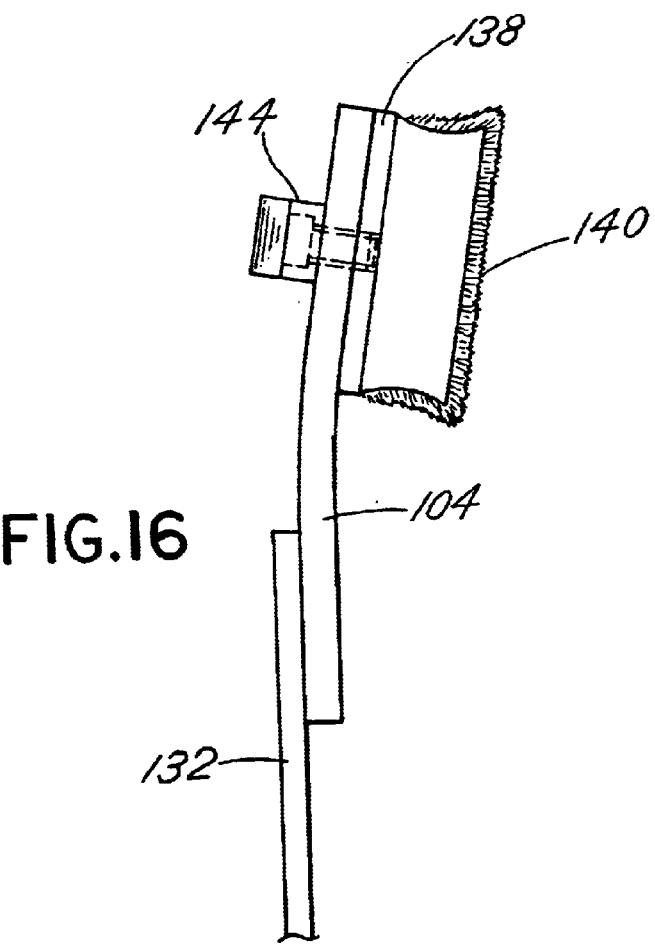

HALO/COLLAR CERVICAL ORTHOSIS

CROSS-REFERENCE TO RELATED APPLICATION

None.

STATEMENT REGARDING FEDERALLY SPONSORED RESEARCH OR DEVELOPMENT

None.

BACKGROUND OF THE INVENTION

The present invention relates to cervical fixation systems for use with patients with cervical or spinal injuries for immobilizing the neck of the patient to promote healing, and bone screws used with such systems.

Cervical collars are orthopedic devices normally applied by a medical practitioner, such as an orthopedic surgeon or neurosurgeon, for immobilizing the patient to promote healing which often takes many months. Collars immobilize the cervical spine by encasing the neck and chin in a rigid foam or foam lined plastic shell. The immobilization of the chin for extended periods of time can be very uncomfortable making talking, eating and carrying on every day tasks very tedious.

Conventional halo vests are also used to immobilize the patient. However, they are more rigid than the collar. The halos are typically comprised of a vest body having front and rear components for overlying the front and back of the patient's torso. The front and rear body components of the halo vest are normally secured to one another by flexible straps around the waist and over the shoulders. Halo support rods attach to the upper portions of the body components for supporting a halo that is secured to the patient's head. The halo is secured by a surgical procedure where four or more pins are driven into the patient's skull. The pins stay in place by using counter-pressure or opposing pin pressure. Around 8 pounds of pressure is applied to each pin thereby driving the pins into the outer surface of the skull and holding the device in place.

Halos are "overkill". They are too bulky and give patients claustrophobia. They are impossible to sleep in and difficult to maneuver (see U.S. Pat. No. 5,261,873). Several problems exist with the use of halo devices, including infection at the pin sites, loosening of the pins and the resulting movement of the halo, penetration of the skull by the pins, and unwanted loading of the halo caused by the shoulder straps which can be moved if the shoulders are elevated.

It is therefore one object of the present invention to eliminate some or all of the problems associated with known halo and/or collar devices, including having to restrict the chin, loosening problems associated with pins, movement of the device caused by shoulder movement, and bulkiness.

It is a further object of the present invention to reduce the problems associated with the penetration of the skull by pins.

It is still a further object of the present invention to reduce the problems caused by the use of pins in present designs by providing a bone screw compatible with present halo designs.

BRIEF SUMMARY OF THE INVENTION

These and other objects of the invention are achieved in a cervical fixation system that immobilizes the patient's head and neck to promote healing. The cervical fixation system comprises a body rigidly attached to a patient's skull at one or more rigid attachment points. In one embodiment, the body comprises a front section and a back section. The front section may be rigidly connected to the back section. In another embodiment, the cervical fixation system comprises a waist belt.

The body of the cervical fixation system is rigidly attached to the patient's skull. One method of achieving a rigid attachment is through the use of bone screws. The bone screw may comprise a shoulder to prevent penetration of the skull. Additionally, the cervical fixation system may comprise a surface configured to meet a bone screw shoulder. In another embodiment, a spacer may be used to prevent penetration.

The bone screw may also attach to the body of the cervical fixation system. In one embodiment, this is accomplished through the use of a quick disconnect head. In another embodiment, the bone screw comprises threads for attachment to the body.

Additionally, a bone screw is provided that may be used with the present claimed cervical fixation system or existing halo devices. The bone screw engages the patient's skull for rigid attachment of the cervical fixation system or halo device to the skull. The bone screw may comprise a threaded body configured to engage the cervical fixation system or halo device, and a distal tip threaded to engage the skull. Alternatively, the bone screw may comprise a quick disconnect head for attachment to the cervical fixation system or halo device.

In one embodiment of the bone screw comprising a threaded body, the distal tip diameter is smaller than the threaded body diameter. In a different embodiment, the distal tip diameter and the threaded body diameter are substantially the same, and the bone screw comprises a threaded bushing and a lock bushing. Still another embodiment comprises an integral bushing.

BRIEF DESCRIPTION OF THE SEVERAL VIEWS OF THE DRAWING

FIG. 10 is an isometric view of a patient fitted with a second embodiment of a cervical fixation system.

FIG. 11 is a back view of a patient fitted with the embodiment of a cervical fixation system illustrated in FIG. 10.

FIG. 12 is a front view of a patient fitted with the embodiment of a cervical fixation system illustrated in FIG. 10.

FIG. 16 is a view of an embodiment of a cervical fixation system with a fleece lining.

FIG. 17 is a back view of an embodiment of a skull plate of a cervical fixation system.

FIG. 18 is a side view of an embodiment of a skull plate of a cervical fixation system.

DETAILED DESCRIPTION OF THE INVENTION

Figure 1:
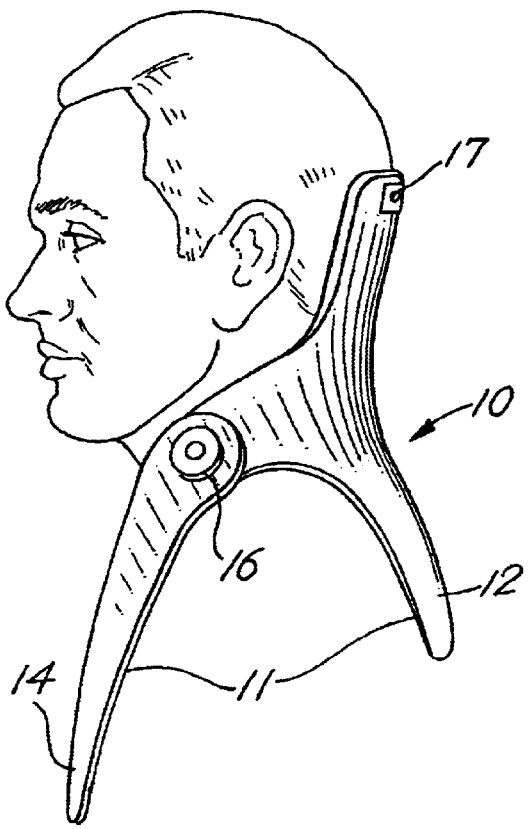
FIG. 1 is a view of the profile of a patient fitted with a first embodiment of a cervical fixation system.
Figure 2:
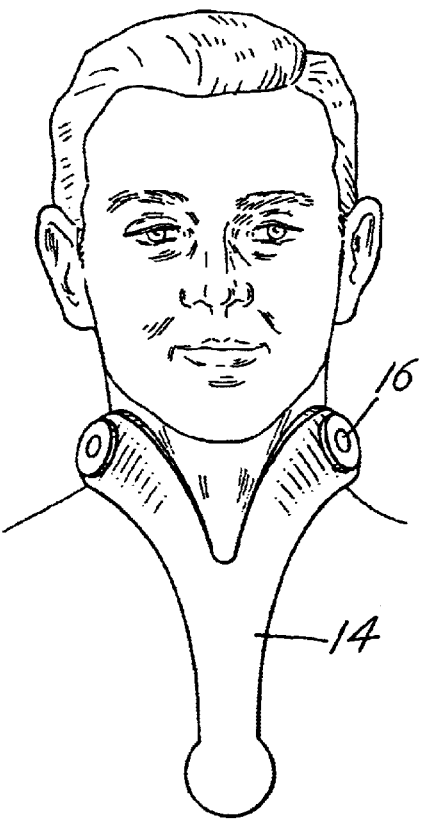
FIG. 2 is a front view of a patient fitted with the first embodiment of a cervical fixation system.
Figure 3:
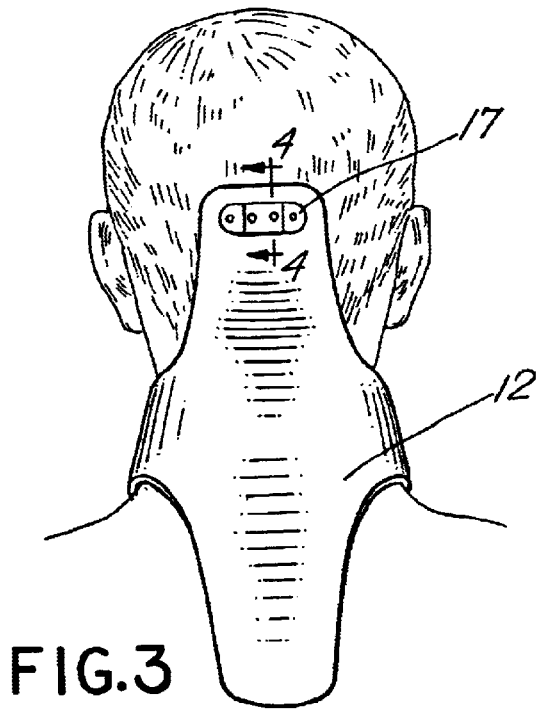
FIG. 3 is a back view of a patient fitted with the first embodiment of a cervical fixation system.

FIGS. 1–3 present different views of one embodiment of the present invention. FIG. 1 shows the profile of a patient with a cervical fixation system 10. FIG. 2 provides a front view, and FIG. 3 is a rear view. The body 11 of the cervical fixation system 10 may be attached to the patient's skull at a rigid attachment point 17. In the illustrated embodiment, the body 11 of the cervical fixation system 10 may be shaped similar to a collar and may comprise a back section 12 and a front section 14 rigidly connected at joints 16. There are two joints 16 located on opposite sides of the patient's neck. In alternate embodiments, the body of the system may be a vest instead of a collar. Such a vest could be similar to those known in the art currently used with halo designs, and may include a waist belt to connect the front and back sections of the vest. Additionally, the body in alternate embodiments may comprise only one piece or may comprise more than two pieces instead of the two-piece body of the illustrated embodiment.

Returning to the illustrated embodiment, the back section 12 is attached to the skull at a rigid attachment point 17. Such an attachment allows the system to properly immobilize the neck while engaging the skull in as few as one or two spots. Thus, the system eliminates problems associated with conventional halo vests such as their bulkiness and claustrophobia-inducing qualities as well as the potential for loosening problems with pins. The attachment of the back section 12 to the skull in such a fashion prevents the patient's head from moving relative to the back section 12. As shown in FIG. 3, the back section 12 extends below the neck of the patient down the back. Thus, pressure from the patient's back resists any attempted movement backward by the patient's head. This prevents backward movement of the patient's head.

As mentioned earlier, the front section 14 of the illustrated embodiment is rigidly attached to the back section 12 at joints 16. Further, as shown in FIG. 2, the front section 14 extends down the chest of the patient. Any attempted forward movement of the patient's head would require a similar movement in the back section 12 because it is attached to the skull. However, because the back section 12 is rigidly connected to the front section 14 which extends down the chest, pressure from the chest plate restricts any such movement. Thus, forward bending (flexion) is prevented.

FIGS. 10–12 present different views of an additional embodiment of the present invention. FIG. 10 shows an isometric view of a patient with a cervical fixation system 100. FIG. 11 provides a rear view, and FIG. 12 is a front view. The cervical fixation system 100 functions similarly to the cervical fixation system 10 previously described, as system 100 also uses rigid attachment points and rigid connections between body components to restrict unwanted movement of the patient's head.

The body 102 of the cervical fixation system 100 comprises a front plate 104, a back plate 108, a skull plate 112, a support bar 114, a back support bar 116, and clamp joints 124. The front plate comprises front clamps 106 which engage the support bar 114. The front plate 104 is joined to the skull plate 112 by the support bar 114. Also, the front plate 104 is joined to the back plate 108 by the support bar 114, the clamp joints 124, and the back support bar 116.

The back support bar 116 comprises back bars 118, pivot joints 120, and connecting bars 122. The back bars 118 meet the connecting bars 122 at the pivot joints 120. The back plate 108 comprises back clamps 110 which engage the connecting bars 122. The back support bar 116 is joined to the support bar 114 by the clamp joints 124. In the illustrated embodiment, the support bar 114 is slidably adjustable in the front clamps 106, the connecting bars 122 are slidably adjustable in the back clamps 110, the back support bar 116 is adjustable both slidably and pivotally relative to the support bar 114 at clamp joints 124, and the back bars 118 and the connecting bars 122 may be pivoted relative to each other at the pivot joints 120. This arrangement provides for improved adjustability and ventilation. Once the desired adjustments have been made to fit the individual patient, the clamps and/or joints may be tightened to provide stability. The front clamps 106, back clamps 110, and clamp joints 124 are typical clamps known to those skilled in the art and are preferably selected to provide complete immobilization between their adjacent components.

The skull plate 112 engages the support bar 114 at a generally-horizontal upper cross position 115. Further, the skull plate 112 is attached to the patient's skull. The specific shape of the skull plate 112 and cooperation between the skull plate 112 and cross bar 114 are not critical so long as these components preferably provide a stable, immobilizing connection between the patient's skull, the skull plate 112 and the cross bar 114.

FIGS. 17 and 18 provide views of the skull plate mounting for one embodiment of the present invention. The skull plate 112 comprises a yoke 144 that is mounted to the skull plate 112 by yoke screws 146. Set screws 148 are used to align the yokes 144 with grooves (not shown) in the support bar 114. Other techniques known in the art, such as key shapes and holes, or other retaining mechanisms, may be used to secure the support bar 114 in the yokes 144 in alternative embodiments.

The skull plate 112 is attached to the skull by the bone screw assemblies 150. The bone screw assembly 150 comprises a bone screw 152 and a spacer 156. The bone screw assembly 150 may optionally comprise washers 154. The spacer 156 holds the skull plate 112 off of the scalp. Additionally, the spacer 156 may be used as a template for drilling the screw hole(s) in the skull. The embodiment illustrated in FIGS. 17 and 18 comprises two bone screw assemblies 150 in a vertical arrangement. Alternatively, different configurations of bone screw assemblies could be used. For example, two bone screw assemblies in a horizontal arrangement could be used. Further, bone screws could be used in combination with pins. For example, configurations featuring two pins and two bone screws, one pin and two bone screws, or one bone screw and three pins could also be used. If one bone screw is used, the spacer 156 may be serrated to help prevent rotation of the skull plate 112.

Figure 13:
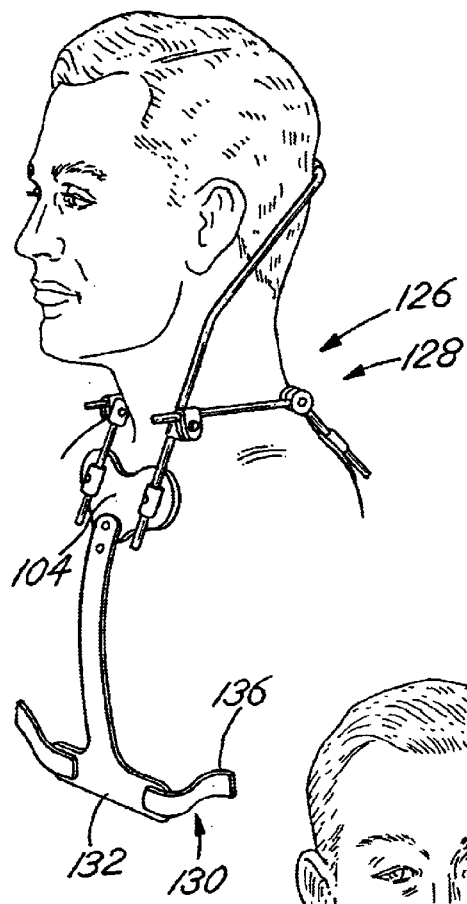
FIG. 13 is an isometric view of a patient fitted with a third embodiment of a cervical fixation system.
Figure 14:
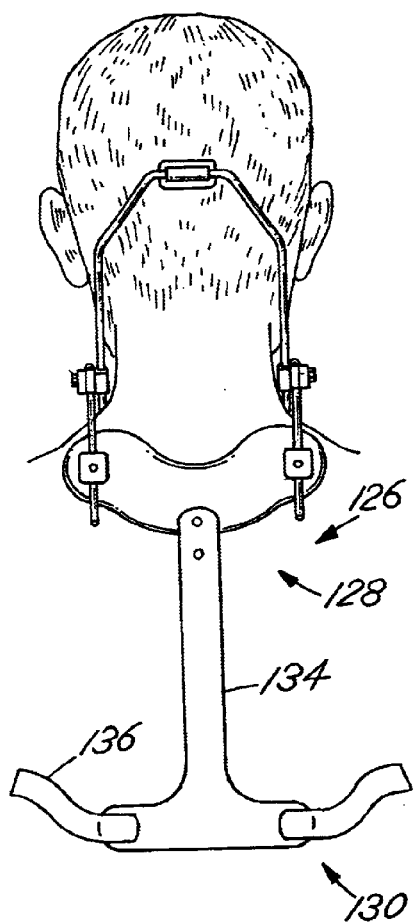
FIG. 14 is a back view of a patient fitted with the embodiment of a cervical fixation system illustrated in FIG. 13.
Figure 15:
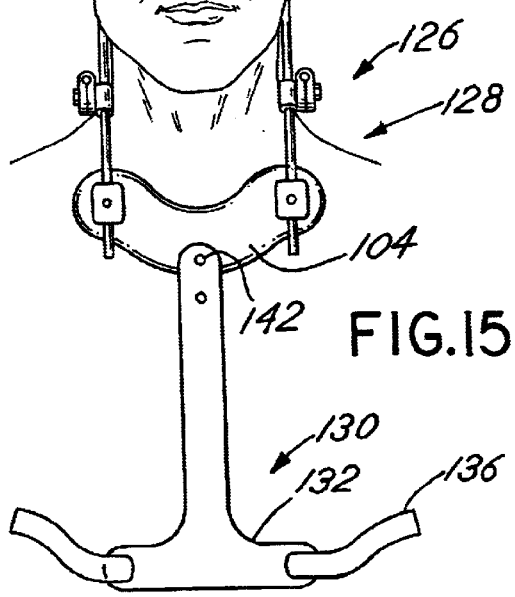
FIG. 15 is a front view of a patient fitted with the embodiment of a cervical fixation system illustrated in FIG. 13.

A further additional alternative embodiment of the present invention is illustrated in FIGS. 13–15. FIG. 13 shows an isometric view of a patient with a cervical fixation system 126. FIG. 14 provides a rear view, and FIG. 15 is a front view. The cervical fixation system 126 is similar in many respects to the cervical fixation system 100 previously described, but the body 128 of the cervical fixation system 126 additionally comprises a belt attachment 130

The belt attachment 130 comprises a front portion 132, a back portion 134, and a belt 136. The front portion 132 of the belt attachment 130 is joined to the front plate 104 of the cervical fixation system 126 by the screw 142. Similarly, the back portion 134 of the belt attachment 130 is joined to the back plate 108 of the cervical fixation system 126. The front portion 132 and the back portion 134 engage the belt 136.

Padding and/or fleece liners may be used to hold the rigid body plates off of a patient's chest and back to make the cervical fixation systems more comfortable to wear. Skin necrosis may be a problem with extended wear if it is not possible to clean under the pads. FIG. 16 illustrates one embodiment of the present invention similar to the embodiment illustrated in FIGS. 13–15 but further incorporating a fleece lining. In the illustrated embodiment, the cervical fixation system comprises a removable pad plate 138, a fleece lining 140, and a pad screw 144. The fleece lining 140 resides between the removable pad plate 138 and the patient's skin. The removable pad plate 138 is joined to the front plate 104 by pad screw 144. The removable pad plate 138 facilitates changing and cleaning of the fleece lining 140. A similar arrangement could be used to provide a fleece lining for the patient's back as well.

Conventional collar designs prevent forward bending by encasing the neck and chin. By preventing forward bending as described above, the illustrated embodiments eliminate the need to encase the chin, making the illustrated cervical fixation systems 10, 100, 126 more comfortable than previous collar designs and making talking and eating much easier for patients.

Pins used with conventional halos only restrict movement along their axes in one direction. Consequently, a number of pins are required to hold the halo in place using counter-pressure or opposing pin pressure. This results in the bulkiness of halos and invites problems with loosening pins. These problems can be avoided by providing a rigid attachment of the body of the cervical fixation system to the skull. Use of a rigid attachment eliminates the need for the use of counter-pressure and allows for attachment at as few as one or two spots instead of a system of pins surrounding the head.

Figure 4:
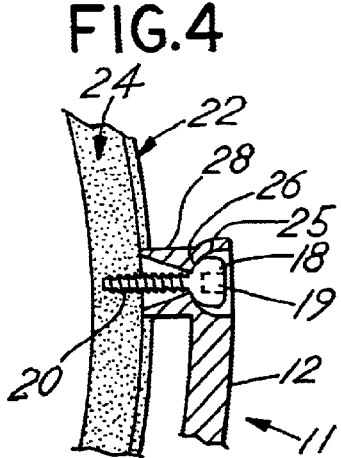
FIG. 4 is a sectional view of a first embodiment of a cervical fixation system and bone screw.

One method that provides such a rigid attachment is the use of bone screws that thread into the skull. FIG. 4 shows one method of using a bone screw with an embodiment of the cervical fixation system. In FIG. 4, the back section 12 of the cervical fixation system is positioned next to the scalp 22. The threaded portion 20 of bone screw 18 engages the skull 24 of the patient. The bone screw 18 may comprise a hex socket head 19 for driving the bone screw 18. Further, the cervical fixation system may comprise a surface 25 configured to meet the shoulder 26 of the bone screw 18. In the illustrated embodiment, shoulder 26 prevents the threaded portion 20 from penetrating the skull 24 by effecting a positive stop when it meets with surface 25. The back section 12 of this embodiment may also include a spacing portion 28 that allows for space between part of the back section 12 and the patient's head to help prevent penetration, and also for comfort, adjustability, and ventilation. Alternatively or additionally, a spacer (not shown) may be placed between the skull 24 and bone screw head 19 to prevent penetration.

In the embodiment illustrated in FIG. 4, a shoulder prevents penetration, and the back section 12 of the cervical fixation system is held against the scalp 22 by tension in a bone screw 18 as the shoulder 26 is brought against a surface 25. Alternatively or additionally, the bone screw 18 may be directly attached to the back section 12. Such a bone screw 18 may also comprise a separate spacer (not shown) placed between the skull 24 and the bone screw head 19 to prevent penetration. A bone screw with a quick disconnect head provides one way to directly attach the bone screw to the back section 12. It is contemplated that current halo designs could be adapted to accept such a bone screw, eliminating the danger of loosening of skull pins.

Figure 5:
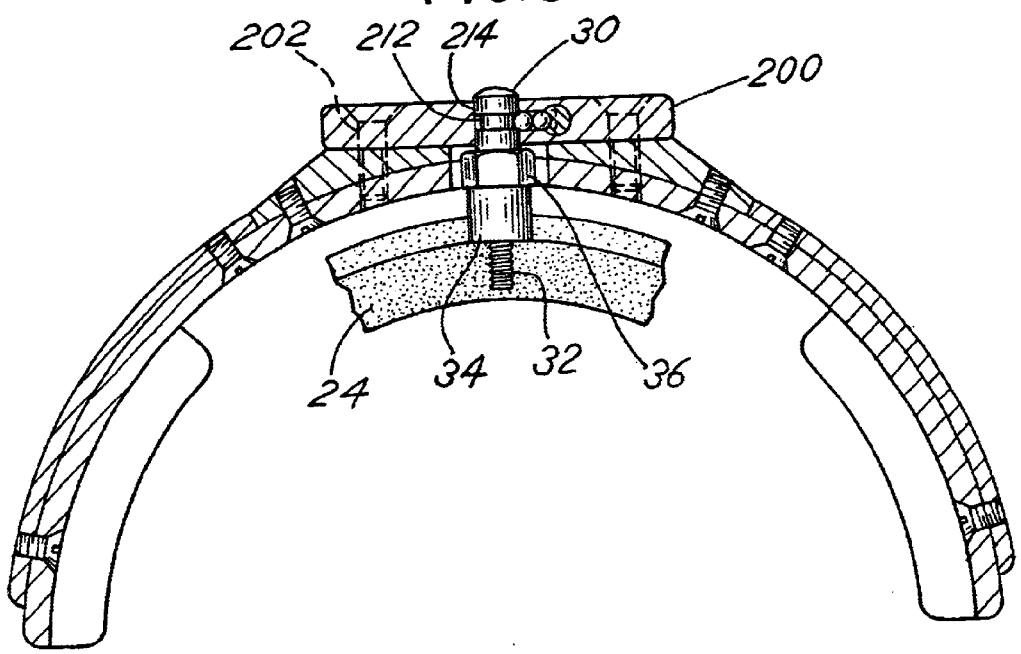
FIG. 5 is a sectional view of a second embodiment of a cervical fixation system and bone screw.
Figure 6:
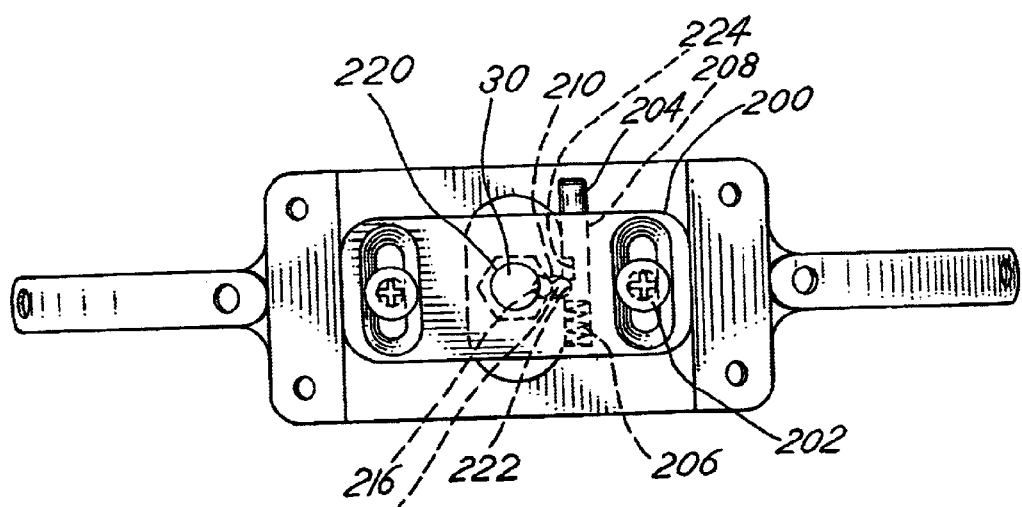
FIG. 6 is an elevation view of the second embodiment of a cervical fixation system and bone screw.

FIGS. 5 and 6 show an embodiment of a cervical fixation system utilizing a bone screw with a quick disconnect head. The embodiment illustrated in FIGS. 5–6 comprises a bone screw 30, a connector plate 200, screws 202, a plunger 204, a spring 206, a first ball 216, and a second ball 218.

The bone screw 30 of this particular embodiment comprises a threaded portion 32, a shoulder 34, a hex surface 36, a screw groove 212, and a bearing surface 214. The threaded portion 32 engages the patient's skull. Shoulder 34 prevents penetration by providing a positive stop against a surface on the skull. Driving the bone screw 30 may be facilitated by the hex surface 36.

The connector plate 200 is mounted to the back section 12 with screws 202. The connector plate 200 comprises a first cylindrical channel 208, a second cylindrical channel 210, and an opening 220. The first cylindrical channel 208 does not pass clear through the connector plate 200 and is disposed orthogonal to the opening 220 but without intersecting the opening 220. The second cylindrical channel 210 is disposed between and connects the opening 220 and the first cylindrical channel 208. The opening 220 is sized to accept the bearing surface 214 of the bone screw 30.

The plunger 204 and the spring 206 are disposed in the first channel 208. In its unbiased state (shown in FIG. 5), the spring 206 retains the plunger 204 in the position shown. The plunger 204 is of a length so that a portion protrudes from the connector plate 200 as shown. The operator may use his or her thumb to press the plunger 204 into the first channel 208 against the force of the spring 206.

A first ball 216 and a second ball 218 are housed in the second channel 210. The proximal end of the second channel 210 where the second channel 210 meets the opening 220 includes an annular stop to prevent the first ball 216 from moving completely into the opening 220. Only a portion of the first ball 216 may move into the opening 220.

The plunger 204 includes a first groove 222 and a second groove 224 which receive the second ball 218. When the first groove 222 engages the second ball 218, the second ball 218 is forced against the first ball 216 driving the first ball 216 to its fullest extent into the opening 220. In this position, the first ball 216 is driven into the screw groove 212, causing the bearing surface 214 of the bone screw 30 to press against the surface of the opening 220. Thus, the bone screw 30 is frictionally retained in place. When the second groove 224 engages the second ball 218, both balls 216, 218 have a larger area into which to move so that the first ball 216 may move fully out of the opening 220.

The pressing of the plunger 204 against the spring 206 moves the second groove 224 into a position to receive the second ball 218. This removes the force of the first ball 216 against the bone screw 30, allowing the connector plate 200 (and the back section 12 to which the connector plate 200 is mounted) to be moved clear of the bone screw 30.

As stated above, the bone screw may be directly attached to the body. Another method of direct attachment is the use of threads on the bone screw that mate with threads in the body of the cervical fixation system. Such a bone screw could be used with the presently claimed cervical fixation system or with current halo devices, eliminating the danger of loosening of skull pins. Additionally, such bone screws may also comprise a separate spacer (not shown) placed between the skull and the bone screw head to prevent penetration.

Figure 7:
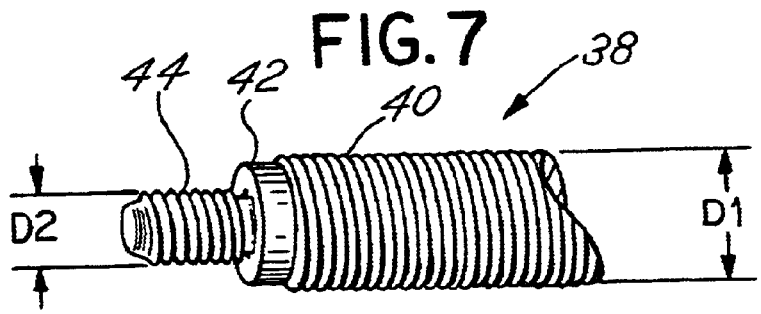
FIG. 7 is a view of a first embodiment of a bone screw for use with cervical fixation systems.

One embodiment of such a bone screw is shown in FIG. 7. In this embodiment, the bone screw 38 is comprised of a threaded body 40, a shoulder 42, and a distal tip 44. The threaded body 40 defines a threaded body diameter D1 and the distal tip 44 defines a distal tip diameter D2. The threaded body 40 has threads that allow for attachment to a halo or other cervical fixation system. The distal tip 44 is threaded for engagement with the patient's skull. Distal tip diameter D2 is smaller than the threaded body diameter D1, thus creating a shoulder 42 where the tip and body meet. This shoulder 42 is drawn up against the skull as the threads on the distal tip 44 engage the skull, thereby preventing penetration. This embodiment may be manufactured from one piece. Further, because the largest diameter of the bone screw 38 is the threaded body diameter D1, bone screw 38 can be threaded through the halo, distal tip 44 first. This allows for the halo or other cervical fixation system to be positioned over the head and then the bone screw 38 to be screwed into the halo or other cervical fixation system and then into the skull.

Figure 8:
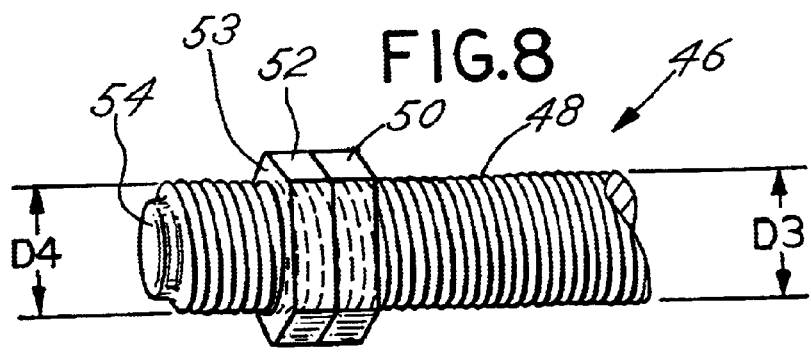
FIG. 8 is a view of a second embodiment of a bone screw for use with cervical fixation systems.

Another embodiment of such a bone screw is shown in FIG. 8. In this embodiment, the bone screw 46 is comprised of a threaded body 48, a threaded bushing 52, a lock bushing 50, and a distal tip 54. Threaded body 48 defines a threaded body diameter D3 and distal tip 54 defines a distal tip diameter D4. The threaded body 48 has threads that allow for attachment to a halo or other cervical fixation system. The distal tip 54 is threaded for engagement with the patient's skull. Distal tip diameter D4 may be substantially the same as threaded body diameter D3. For simple and inexpensive manufacture, the threads of the distal tip 54 and the threaded body 48 may be identical. For such an embodiment, the bone screw could be comprised of a single threaded rod, threaded bushing 52, and lock bushing 50. Threaded bushing 52 and lock bushing 50 are threaded in place after the bone screw 46 has been threaded into the halo or other cervical fixation system but before the bone screw 46 engages the skull. They thereby form a shoulder 53 that is drawn up against the skull as the threads on the distal tip 54 engage the skull, thereby preventing penetration. This embodiment allows for adjustability of the length of threads allowed to engage the skull as well as for a larger diameter of threads engaging the skull. Further, because the threaded bushing 52 and lock bushing 54 are positioned after the bone screw is screwed into the halo or other cervical fixation device, bone screw 46 can be threaded through the halo, distal tip 54 first. This allows for the halo or other cervical fixation device to be positioned over the head and then the bone screw 46 to be screwed into the halo or other cervical fixation device and then into the skull.

Figure 9:
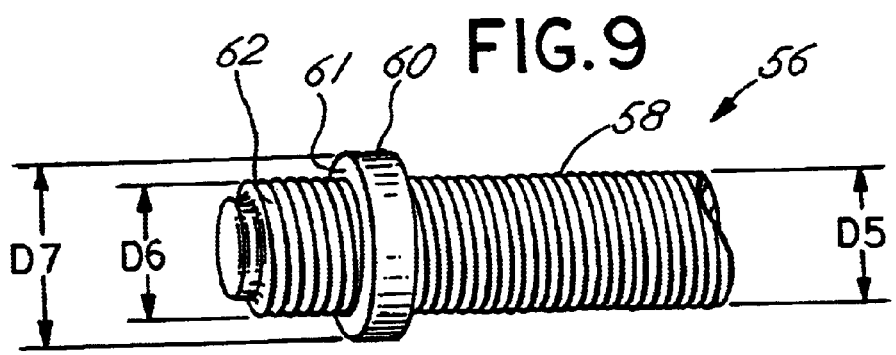
FIG. 9 is a view of a third embodiment of a bone screw for use with cervical fixation systems.

Yet another embodiment of such a bone screw is shown in FIG. 9. In this embodiment, the bone screw 56 is comprised of a threaded body 58, a bushing 60, and a distal tip 62. The threaded body 58 has threads that allow for attachment to a halo or other cervical fixation system. The distal tip 62 is threaded for engagement with the patient's skull. The bushing 60 is an integral part of the bone screw 56. Threaded body 58 defines a threaded body diameter D5, distal tip 62 defines a distal tip diameter D6, and bushing 60 defines a bushing diameter D7. Bushing diameter D7 is larger than distal tip diameter D6, thus forming a shoulder 61 that is drawn up against the skull as the threads on the distal tip 62 engage the skull, thereby preventing penetration. This embodiment may be manufactured from one piece.

The bone screws of any embodiment may be made from materials known in the art. Preferably, at least the distal tip will be made of a material that does not corrode significantly. Examples of such materials include stainless steel, titanium, biologically compatibly ceramic material (such as single crystal alumina ceramic), or a suitable gemstone (such as sapphire).

Other components of the systems described above may be made from these same materials or other materials familiar to those skilled in the art.

While particular embodiments of the invention have been shown, it will be understood that the invention is not limited thereto since modifications may be made by those skilled in the art, particularly in light of the forgoing teaching. It is, therefore, the appended claims that define the true spirit and scope of the invention.

What is claimed is:

1. An external cervical fixation system comprising a body and one or more bone screws, said body adapted for rigid attachment to a patient's skull at one or more rigid attachment points with said one or more bone screws, said bone screw comprising a threaded distal tip adapted for threaded engagement with a patient's skull.

2. The cervical fixation system of claim 1 wherein said body is adapted for rigid attachment to a patient's skull with one or more bone screws and one or more skull pins.

3. The cervical fixation system of claim 1 wherein said body comprises a front section and a back section.

4. The cervical fixation system of claim 3 wherein said body is adapted for rigid attachment to a patient's skull with one or more bone screws.

5. The cervical fixation system of claim 3 wherein said front section is rigidly connected to said back section.

6. The cervical fixation system of claim 5 wherein said body is adapted for rigid attachment to a patient's skull with one or more bone screws.

7. The cervical fixation system of claim 1 wherein said bone screw comprises a shoulder.

8. The cervical fixation system of claim 7 where said body comprises a surface configured to meet said shoulder as said bone screw engages a patient's skull.

9. The cervical fixation system of claim 1 wherein said cervical fixation system further comprises a waist belt.

10. The cervical fixation system of claim 1 wherein said bone screw attaches to said body.

11. The cervical fixation system of claim 10 wherein said bone screw comprises a quick disconnect head for attachment to said body.

12. The cervical fixation system of claim 10 wherein said bone screw comprises threads for attachment to said body.

13. The cervical fixation system of claim 1 wherein said cervical fixation system further comprises a spacer located proximal to said threaded distal tip to prevent penetration.

14. A bone screw for use with a cervical fixation system comprising:
  a threaded body adapted to engage a cervical fixation system, said threaded body defining a threaded body diameter;
  a threaded distal tip, said distal tip adapted for threaded engagement with a patient's skull, said threaded distal tip defining a distal tip diameter; and
  a spacer located proximal to said threaded distal tip and adapted to prevent penetration through the patient's skull.

15. The bone screw of claim 14, wherein said distal tip diameter is smaller than said threaded body diameter.

16. The bone screw of claim 14, wherein said bone screw further comprises a threaded bushing and a lock bushing.

17. The bone screw of claim 16, wherein said distal tip diameter is substantially the same as said threaded body diameter.

18. The bone screw of claim 14, wherein said bone screw further comprises an integral bushing.

19. The bone screw of claim 14, wherein said bone screw comprises a quick disconnect head.

20. The bone screw of claim 19 wherein said bone screw further comprises a spacer located proximal to said threaded distal tip and adapted to prevent penetration of a patient's skull.

* * * * *